(12) United States Patent
Segarra et al.

(10) Patent No.: US 8,859,298 B2
(45) Date of Patent: Oct. 14, 2014

(54) NANOBEADS COVERED WITH PLASMINOGEN AS A DIRECT SUPPORT FOR CYCLIC AMPLIFICATION OF THE PRION PROTEIN PRP$^{SC}$

(75) Inventors: Christiane Segarra, Claret (FR); Joliette Coste Van Der Luur, Montpellier (FR); Daisy Bougard, Gigean (FR)

(73) Assignee: Etablissement Francais du Sang, La Plaine Saint Denis Cedex (FR)

( * ) Notice: Subject to any disclaimer, the term of this patent is extended or adjusted under 35 U.S.C. 154(b) by 0 days.

(21) Appl. No.: 13/425,806

(22) Filed: Mar. 21, 2012

(65) Prior Publication Data

US 2012/0244559 A1 Sep. 27, 2012

Related U.S. Application Data

(60) Provisional application No. 61/454,727, filed on Mar. 21, 2011.

(30) Foreign Application Priority Data

Mar. 21, 2011 (FR) ...................................... 11 52298

(51) Int. Cl.
*G01N 33/553* (2006.01)
*G01N 33/543* (2006.01)
*G01N 33/68* (2006.01)

(52) U.S. Cl.
CPC ...... *G01N 33/6896* (2013.01); *G01N 33/54346* (2013.01); *G01N 2333/968* (2013.01); *G01N 2800/2828* (2013.01); *G01N 33/54326* (2013.01)
USPC .......................................... 436/525; 436/526

(58) Field of Classification Search
None
See application file for complete search history.

(56) References Cited

U.S. PATENT DOCUMENTS

| | | | | |
|---|---|---|---|---|
| 7,699,979 | B2 * | 4/2010 | Li et al. ..................... | 210/138 |
| 2002/0004586 | A1 * | 1/2002 | Aguzzi et al. .............. | 530/388.2 |
| 2004/0137523 | A1 * | 7/2004 | Vodyanoy et al. ............. | 435/7.1 |
| 2004/0209282 | A1 * | 10/2004 | Ault-Riche et al. ............... | 435/6 |
| 2005/0191665 | A1 * | 9/2005 | Su et al. ............... | 435/6 |
| 2009/0176258 | A1 | 7/2009 | Latza | |
| 2009/0227044 | A1 * | 9/2009 | Dosev et al. .................. | 436/526 |
| 2013/0260367 | A1 * | 10/2013 | Lowery et al. ................... | 435/5 |

FOREIGN PATENT DOCUMENTS

| | | |
|---|---|---|
| EP | 1 435 521 | 7/2004 |
| WO | WO-02/00713 | 1/2002 |
| WO | WO 03/073106 A2 * | 9/2003 ............. G01N 33/68 |

OTHER PUBLICATIONS

Fischer, M.B. et al., "Binding of disease-associated prion protein to plasminogen", Nature (2000), 408:479-483.*
Guntz, P. et al "Feasibility study of a screening assay that identifies the abnormal prion protein PrPtse in plasma: initial results with 20,000 samples", Transfusion (2010), 50:989-995.*
Jones, M. et al., "Human platelets as a substrate source fo the in vitro amplification of the abnormal prion protein (PrPsc) associated with variant Creutzfeldt-Jakob diesease" Transfusion (2009) 49:376-384.*
Miller, M.B. et al., "Superparamagnetic nanoparticle capture of prions for amplification" J. Virology (2011), 85(6):2813-2817.*
Fischer, M.B. et al., "Binding of disease-associated prion protein to plasminogen", Nature (2000) 408:479.*
Written Opinion from corresponding French Application No. FR 1152298.
M.B. Miller, et al, "Superparamagnetic Nanoparticle Capture of Prions for Amplification", Mar. 15, 2011, pp. 2813-2817, vol. 85, No. 6, Journal of Virology.
Mays, et al, "Plasminogen Stimulates a propagation of protease-resistant prion protein in vitro", Dec. 2010, pp. 5102-5112, vol. 24, No. 12, The Faseb Journal: Official Publication of the Federation of American Societies for Experimental Biology.
Massimilano et al, "Binding of recombinant human PrPc to human plasminogen: Kinetic and thermodynamic study using a resonant mirror biosensor", Feb. 15, 2005, pp. 728-734, vol. 58, No. 3, Proteins: Structure, Function and Bioinformatics.
Bougard, et al., "A Confirmatory Assay for the Presence of PrP$^{TSE}$ Protein in Human Plasma"—Abstract Vox Sanguinis (2010) 99(Suppl.1):319.
Segarra, et al., "Development of a Confirmatory Assay for the Presence of Prion Protein in Plasma"—Abstract Clinique and Biologique (2009) 16(3):295.

* cited by examiner

*Primary Examiner* — Chris L Chin
*Assistant Examiner* — Gary E Hollinden
(74) *Attorney, Agent, or Firm* — Stephen J. Weyer, Esq.; Stites & Harbison, PLLC.

(57) ABSTRACT

The present invention relates to an in vitro method for detecting a pathogenic conformational isomer of the prion protein in a sample, said method comprising a preliminary step for capturing the pathogenic conformational isomer by putting the sample into contact with nanobeads covered with a ligand of the pathogenic conformational isomer, and then applying a cyclic amplification of the misfolded prion protein directly on the solid support having captured the pathogenic conformational isomer, and detecting the presence of the pathogenic conformational isomer. The invention also relates to a kit for applying this method and to a method for decontaminating a biological sample.

18 Claims, No Drawings

NANOBEADS COVERED WITH PLASMINOGEN AS A DIRECT SUPPORT FOR CYCLIC AMPLIFICATION OF THE PRION PROTEIN PrP$^{SC}$

CROSS REFERENCE TO RELATED APPLICATIONS

This application claims benefit of U.S. Provisional Application No. 61/454,727, filed Mar. 21, 2011 (which are hereby incorporated by reference).

The present invention relates to an in vitro method for detection of a pathogenic conformational isomer of the prion protein in a sample, said method comprising a preliminary step for capturing the pathogenic conformational isomer by putting the sample into contact with nanobeads covered with a ligand of the pathogenic conformational isomer, and then the application of cyclic amplification of the misfolded prion protein directly on the solid support having captured the pathogenic conformational isomer, and the detection of the presence of the pathogenic conformational isomer. The invention also relates to a kit for application of this method and to a method for decontaminating a biological sample.

Conformational diseases form a group of diseases which are not related to each other but which share the same molecular mechanisms involving a conformational transition of an existing protein (non-pathogenic conformational isomer) to aberrant folding (pathogenic conformational isomer) leading to protein aggregations and to the formation of tissue deposits.

Typical examples of these diseases are transmissible spongiform encephalopathies and Alzheimer's disease. Transmissible spongiform encephalopathies are relatively rare in humans but have been subject of particular attention when the risks of transmission of the bovine form of spongiform encephalopathy to humans were revealed through the food chain. The variant of Creutzfeldt-Jacob's disease (vCJD) is the human counterpart of bovine spongiform encephalopathy.

At the beginning of the year 2010, 246 primary cases of vCJD have been listed in 11 different countries. Although clinical incidence of vCJD remains low, the overall prevalence of the disease at the preclinical stage is evaluated to be 1:4000 in the United Kingdom. The normal cell prion protein) (PrP$^C$), undergoing a conformational transition towards an abnormally folded pathogenic conformational isomer (PrP$^{SC}$), is at the origin of transmissible spongiform encephalopathies. The protein PrP$^{SC}$ is mainly found at the brain and at lymphoid organs of infected animals, but it may also be detected in many tissues including skeletal muscle, the liver, pancreas, kidneys, uterus, and the skin.

This peripheral distribution of PrP$^{SC}$ poses the problem of the potential inter-individual transmission of the variant of CJD, by surgery or invasive medical procedure, such as blood transfusion or transplantations.

It is therefore particularly important to be able to substantially and specifically detect blood donations which will have been collected from patients affected with the variant of Creutzfeldt-Jacob's disease. Sanitary control of foodstuffs of animal origin (milk, meats) is also important.

More generally, the development of a highly sensitive and specific method for detecting pathogenic conformational isomers of prion diseases has usefulness for diagnosing these diseases in patients, in particular when they are still in an asymptomatic phase.

The capability of the prion protein PrP$^{SC}$ of catalyzing the transformation of the non-pathogenic conformational isomer into a pathogenic conformational isomer was exploited in order to develop a method for detecting pathogenic conformational isomers by cyclic amplification. This technology, called <<Protein Misfolding Cyclic Amplification>> (PMCA) was initially described by Saborio et al. (Nature, 2001, 401(6839):810-3). Cyclic amplification is based on the conversion of a substrate consisting of non-pathogenic conformational isomers by undetectable amounts of pathogenic conformational isomers, so as to obtain detectable levels of pathogenic conformational isomers with conventional methods such as immunoblots. This is made possible by repeating incubation cycles of the pathogenic conformational isomer in the presence of the non-pathogenic conformational isomer, with which the amount of pathogenic conformational isomer may be increased, followed by disaggregation of the formed aggregates, so as to make the pathogenic conformational isomers accessible in order to catalyze the conversion of new non-pathogenic conformational isomers.

However, cyclic amplification of the protein PrP$^{SC}$ directly from blood remains difficult, notably because of the large volumes of samples required for allowing detection and because of the presence of inhibitors of the protein PrP$^{SC}$ in the blood.

In order to find a remedy to these problems, the inventors sought to develop an improved PMCA methodology, with a preliminary step for concentrating the protein PrP$^{SC}$.

Tests conducted using sodium phosphotungstate or streptomycin sulfate, if they actually led to a concentration of the protein PrP$^{SC}$, did not then allow efficient amplification of the pathogenic conformational isomer PrP$^{SC}$ by PMCA.

The inventors managed to develop an extremely sensitive method for detecting the protein PrP$^{SC}$, based on the capture of the pathogenic conformational isomer of the prion protein present in the sample to be analyzed, by means of a solid support consisting of nanobeads covered with plasminogen, followed by direct amplification of the pathogenic conformational isomer bound to the solid support by PMCA, and then detection of the amplified pathogenic conformational isomers.

Recently, it has been described that superparamagnetic iron oxide nanoparticles have the capability of selectively binding the protein PrP$^{SC}$ (Miller and Supattapone, J. Virol. 2011 Jan. 12. [Epub ahead of print]). The capability of the protein PrP$^{SC}$ of binding nanoparticles was revealed by applying a PMCA amplification cycle directly on the nanoparticles which had bound PrP$^{SC}$. This article suggested that the application of a concentration step by binding PrP$^{SC}$ with the magnetic nanoparticles, coupled with PMCA, might improve detection of low concentrations of prion proteins. The amplification levels shown after 72 hours of PMCA however remain very low, 5 µl of 5% brain not giving any signal without PMCA and a very low signal with PMCA for the RML strain of CD1 mice, and a low signal for hamster 237 strain.

Moreover it was reported that plasminogen acts as a cofactor stimulating conversion of the protein PrP$^C$, the production rate of PrP$^{SC}$ being multiplied by about 2.5 in the presence of 0.5 µM of human plasminogen in the reaction medium of PMCA (Mays and Ryou, Prion. 2011; 5(1):22-7; Mays and Ryou, FASEB J. 2010; 24(12):5102-12).

The principle of the application of a PMCA amplification after concentration of the protein PrP$^{SC}$ by means of beads covered with a ligand of the protein PrP$^{SC}$ was described by the inventors (Transfusion Clinique et Biologique 2009, 16(3): 295), without however identifying the nature of the ligand used.

Now, several types of ligand of the protein PrP$^{SC}$ have been identified and notably include aptameric nucleic acids (Sayer et al., J. Biol. Chem. 2004, 279(13):13102-13109), anti-DNA antibodies (Zou et al., Proc. Natl. Acad. Sci. USA, 2004, 101:1380-1385), monoclonal anti-PrP$^{SC}$ antibodies (Korth et al., Nature 1997, 390: 74-77, and Paramithiotis et al., Nat. Med. 2003, 9: 893-899) and polyanionic ligands (International Patent Application WO 03/073106).

The inventors thus demonstrated unexpectedly that the plasminogen bound to nanobeads allows binding of pathogenic conformational isomers PrP$^{SC}$ and that the latter remain accessible for converting non-pathogenic conformational isomers PrP$^C$ into pathogenic conformational isomers PrP$^{SC}$.

The specificity of the plasminogen for the protein PrP$^{SC}$ is controversial, the plasminogen having both been reported to exclusively bind the protein $PrP^{SC}$ (see for example Fischer et al. Nature 2000, 408(6811):479-483; Maissen et al., The Lancet, 2001, 357(9273):20262028)) while other investigations have shown that the plasminogen also bound the protein $PrP^{C}$ (Cuccioloni et al., Proteins 2005; 58(3):728-734).

Without having clarified whether the beads covered with plasminogen only captured the protein $PrP^{SC}$ or also normal PrP isoforms from samples to be analyzed, the inventors made the assumption that the presence of residual $PrP^{C}$ in addition to the protein pathogenic conformational isomer $PrP^{SC}$ did not represent a major problem considering the fact that cyclic amplification of the misfolded proteins conducted subsequently uses the protein $PrP^{C}$ as a substrate for amplifying the protein $PrP^{SC}$.

The application of the method of the inventors on plasmas doped with homogenates of infected brain from transgenic mice models of sheep scrapie (line tg 338) allow detection of the protein $PrP^{SC}$ in dilutions by a factor of $10^{-10}$ of homogenates of infected brains, corresponding to the equivalent of an initial amount of 10 pg of brain. A higher sensitivity than the one obtained by a biotest carried out on the same strain was thereby obtained (dilution $10^{-8}$; Tixador et al., PLoS Pathog 2010, 6(4:e1000859)). The sensitivity of the thereby developed method would correspond to less than 0.01 time the average lethal dose. The method of the inventors applied to the detection of the prion protein in sheep white cells has 100% sensitivity.

Moreover, it was shown that the capture step is essential, when the method is applied on blood samples, in order to be able to detect the protein $PrP^{SC}$ in infectious samples, PMCA carried out without any preliminary capture leading to false negative results.

The method applied to the detection of the variant of human Creutzfeldt-Jacob's disease allowed detection of the human protein $PrP^{SC}$ in human plasma samples added with homogenates of infected brains with the equivalent of an initial amount as low as 100 pg of brain.

As compared with the methodology of cyclic amplification of misfolded proteins described by Jones et al. (Transfusion 2009, 49(2):376-84), which detected the protein $PrP^{SC}$ by using platelets as an amplification substrate, the method according to the present application gave the possibility of obtaining 100 times higher sensitivity.

The in vitro method for detection of a pathogenic conformational isomer of a protein characteristic of a conformational disease described in the present application is therefore an unquestionable improvement relative to detection methods available today.

Definitions

The term of <<conformational disease>> designates a set of diseases characterized by protein aggregation and tissue deposition phenomena related to the conformational transition of a protein, characteristic of the conformational disease, between a normal non-pathogenic conformational isomer and a pathogenic conformational isomer.

Conformational diseases notably include transmissible spongiform encephalopathies.

Transmissible spongiform encephalopathy (TSE) designates the human forms of TSE, in particular Creutzfeldt-Jacob's disease (CJD) or its variant (vCJD), kuru disease, Gerstmann-Straussler-Scheiker's disease (GSS) and fatal familial insomnia (FFI), and animal forms of TSE, in particular sheep scrapie, bovine spongiform encephalopathy (BSE), transmissible mink encephalopathy (TME) and chronic wasting disease (CWD) in cervids. A transmissible spongiform encephalopathy is preferably CJD or its variant, still preferably vCJD.

By <<characteristic protein of a conformational disease>>, is meant a protein which normally exists as a non-pathogenic conformational isomer in a healthy individual and which may undergo a conformational transition leading to abnormal folding (pathogenic conformational isomer). The pathogenic conformational isomer is generally insoluble and forms aggregates. The pathogenic conformational isomer has the capability of specifically interacting with the non-pathogenic conformational isomer and of catalyzing its conversion into a pathogenic conformational isomer, thereby ensuring propagation of the conformational transition of the pathogenic conformational isomer to the non-pathogenic conformational isomer.

The characteristic protein of transmissible spongiform encephalopathies is the prion protein (PrP), the non-pathogenic conformational isomer of which is generally designated as $Prp^{C}$ and the pathogenic conformational isomer $PrP^{SC}$ or $PrP^{TSE}$.

A Method for Detecting a Pathogenic Conformational Isomer of the Prion Protein

The invention relates to a method for detecting a pathogenic conformational isomer of the prion protein which includes a step for concentrating the abnormal conformational isomer by capturing the abnormal conformational isomer present in a sample to be analyzed by means of a ligand of the abnormal conformational isomer, the plasminogen, bound on a solid support consisting of nanobeads, a step for cyclic amplification of misfolded prion proteins then being directly applied on the solid support having bound abnormal conformational isomer molecules.

The invention therefore relates to a in vitro method for detection of a pathogenic conformational isomer of the prion protein ($PrP^{SC}$) in a sample, said method comprising the steps of:

a) putting nanobeads covered with plasminogen into contact with a sample;

b) separating said nanobeads covered with plasminogen from the sample;

c1) putting said nanobeads covered with plasminogen obtained in step b) into contact with a preparation comprising some non-pathogenic conformational isomer of the prion protein)($PrP^{C}$);

c2) disaggregating the possibly formed aggregates during step c1);

d) detecting the presence of $PrP^{SC}$ in the preparation, the presence of $PrP^{SC}$ in the preparation being indicative of the presence of $PrP^{SC}$ in the sample;

steps c1) and c2) forming a cycle which is repeated at least twice before applying step d).

A sample to be analyzed in the sense of the invention may be any food fluid or solid, in particular of animal origin, such as milk, meat and any biological sample from a human or animal subject.

The term of <<subject>> designates a human or non-human mammal such as a bovine, an ovine, a porcine, a cervid, a feline, a canine, a rodent, a mink.

A <<biological sample>> may designate a biological fluid, cells or a tissue, such as for example blood, lymph, urine, milk, brain tissue, spinal cord, lymphoid tissues or cells, or any product derived from a human or animal source which may be contaminated by a pathogenic conformational isomer such as, for example a growth hormone preparation or a tissue extract. A biological sample may also designate a blood, plasma sample or an organ intended to be transplanted.

When the sample is a tissue, the method according to the invention may be applied on a homogenate of the tissue.

By <<nanobeads>> are designated beads with a diameter comprised between 1 and 900 nm, preferably between 10 and 750 nm, still preferably between 30 and 500 nm, still preferably between 50 and 300 nm or further between 75 and 150 nm.

The nanobeads are preferably paramagnetic. Paramagnetic nanobeads generally contain a high percentage of iron oxides, for example at least 50% by weight, or further at least 70% by weight. Paramagnetic nanobeads commercially available such as for example those distributed by Ademtech (France), may be used for applying the invention. These may in particular be superparamagnetic carboxylic nanobeads such as the Carboxyl-Adembeads of Ademtech.

Without intending to be bound by this theory, the inventors believe that the use of paramagnetic nanobeads is important for applying the method according to the invention, since the nanobeads, by constantly repelling each other because of their paramagnetism, would remain longer suspended, thereby promoting accessibility of the captured proteins $PrP^{SC}$ to the proteins $PrP^C$ of the PMCA reaction mixture. Indeed, tests conducted with microbeads were not able to obtain satisfactory amplification of the captured proteins $PrP^{SC}$ when the incubation steps are carried out in the absence of stirring.

The nanobeads are covered with plasminogen, and optionally with at least one other type of ligand of the pathogenic conformational isomer of the prion protein.

The plasminogen is preferably human plasminogen.

A <<ligand of a pathogenic conformational isomer of the prion protein>> is a molecule which may be of any nature, for example a peptide, a protein, a nucleic acid, a lipid, an ion, etc., and which is capable of binding a pathogenic conformational isomer of the prion protein. The ligand may bind the pathogenic conformational isomer preferentially to the non-pathogenic conformational isomer, still preferably it may specifically bind the pathogenic conformational isomer. The fact that the ligand may both bind the pathogenic conformational isomer and the non-pathogenic conformational isomer is not limiting for applying the invention since the step for capturing the pathogenic conformational isomer is then followed by cyclic amplification of misfolded proteins during which the non-pathogenic conformational isomer makes up the amplification substrate. A preferential or specific bond of the ligand to the pathogenic conformational isomer, relatively to the non-pathogenic conformational isomer, is however preferable so as to avoid saturation of the solid support with a non-pathogenic conformational isomer portion, with the risk of reducing the capture efficiency for the pathogenic conformational isomer from the sample to be analyzed.

A ligand of the pathogenic conformational isomer $PrP^{SC}$ may be selected from the group consisting of aptameric nucleic acids (see in particular Sayer et al., J. Biol. Chem. 2004, 279(13):13102-13109), anti-DNA antibodies (see in particular Zou et al., Proc. Natl. Acad. Sci. USA, 2004, 101: 1380-1385), monoclonal anti-$PrP^{SC}$ antibodies (see for example Korth et al., Nature 1997, 390: 74-77, and Paramithiotis et al., Nat. Med. 2003, 9: 893-899) and polyanionic ligands.

Suitable polyanionic ligands were described in International Patent Application WO 03/073106, and notably include polyanionic polyglycosides, in particular polysulfone polyglycosides, preferably pentosan polysulfate or dextran sulfate; polyethylene imines; polyamines, notably polylysines; polyamidoamines, for example poly(amidoamine) dendrimers; and quaternary polyamines such as poly(diallyldimethylammonium chloride) or polybrene (or 1,5-dimethyl-1,5-diazaudecamethylene, polymethobromide, or hexadimethrin bromide). This type of ligands was described as binding the $PrP^{SC}$, β-amyloïd and tau proteins.

The aptamers form a class of molecules which represent an alternative to antibodies in terms of molecular recognition. Aptamers are sequences of nucleic acids having the capability of practically recognizing any class of target molecules with high affinity and specificity. Such ligands may be isolated by a screening called SELEX (Systematic Evolution of Ligands by EXponential enrichment) of a bank of random sequences, as described in Tuerk et Gold (Science. 1990 3; 249(4968): 505-10). The random sequence bank may be obtained by DNA synthesis through combinatorial chemistry. In such a bank, each member is a linear, optionally chemically modified oligomer, corresponding to a unique sequence. The possible modifications, applications and advantages of this class of molecules have been the subject of a review by Jayasena (Clin Chem. 1999 45(9):1628-50). The aptamers may also be of peptide nature. They consist in a conformationally constrained variable region assembled on a protein platform, such as Thioredoxin A of E. coli, and may be selected from combinatorial banks by two-hybrid methods (Colas et al., Nature 1996, 380, 548-50.).

The plasminogen, and optionally the ligand of the pathogenic conformational isomer of the prion protein may be bound on paramagnetic nanobeads by any means known to one skilled in the art, by a direct or indirect bond, for example by a physical (heat pressure) means or a chemical means by creating covalent or non-covalent (hydrophobic, anionic) bonds via reactive groups of the carboxyl, amine type or passively, for example if the ligand is a polyanionic material and the solid support consists of polystyrene, etc.

In step a) of the method according to the invention, the nanobeads covered with plasminogen are put into contact with the sample to be analyzed. The nanobeads are incubated in contact with the sample for a sufficient time and under conditions allowing binding to the plasminogen of all or part of the pathogenic conformational isomers $PrP^{SC}$ present in the sample.

The duration and the incubation conditions may be variable depending on the nature of the sample. The conditions and incubation time will preferably be determined so that the plasminogen bound on the nanobeads may bind a maximum of pathogenic conformational isomer $PrP^{SC}$.

The incubation may be carried out at any temperature, for example at a cold temperature (4-10° C.), at room temperature or at 37° C. It is preferentially applied at 37° C. The incubation may be carried out with stirring (for example from 1 rpm to 1,400 rpm) or without stirring. The incubation may be carried out for a duration from 1 minute to 5 days, preferably for 5 minutes to 24 hours, preferably 10 minutes to 4 hours, preferably 30 minutes to 3 hours, still preferably from 1 hour to 2 hours. The incubation time may be adjusted depending on the respective amounts of pathogenic conformational isomer of the prion protein in the sample and of plasminogen bound on the solid support.

Optimization of the capture parameters gave the possibility of attaining a capture efficiency with a yield above 95%. For this, crossed tests were carried out between the amount of beads to be used for the capture in 500 µl of plasma and the plasminogen concentration required for functionalizing the nanobeads. The tests conducted over a wide range of both components gave the possibility of observing that the amounts of nanobeads and the plasminogen concentration had to be defined very finely for optimum capture. Indeed, unlike popular belief, the maximum amounts are not the most efficient. Thus, in the case of paramagnetic carboxylic nanobeads (Ademtech, France), optimum amplification is obtained when the beads are functionalized with a plasminogen amount corresponding to the minimum amount of protein recommended by the nanobead supplier.

Thus, preferably, the nanobeads, in particular paramagnetic nanobeads, used within the scope of the invention, are covered with plasminogen in an amount of 10 to 30 µg of plasminogen per mg of nanobeads, more preferably in an amount of 10 to 20 µg of plasminogen per mg of nanobeads, most preferably in an amount of 10 µg of plasminogen per mg of nanobeads.

In the same way for volumes of paramagnetic carboxylic nanobeads functionalized with plasminogen used for the capture, the optimum signal is obtained with 10 µl of 1% nanobeads (i.e. 10 µl of a suspension of nanobeads with 1 mg of nanobeads per ml of suspension). A signal decay is observed when 20 µl are used and finally the signal disappears when capture is achieved with 30 µl of nanobeads functionalized by the plasminogen. Also, when decreasing amounts of nanobeads functionalized by plasminogen are used, the signal decreases more and more when 5 µl of nanobeads are used for the capture and subsequently with 2.5 µl of nanobeads.

Thus, preferably, the nanobeads covered with plasminogen are put, in step a) of the method according to the invention, into contact with a sample at a ratio of 2.5 to 90 µl of a 1% nanobead suspension (weight/volume) for 50 to 500 µl of sample, more preferably a ratio from 5 to 50 µl of a 1% nanobead suspension (weight/volume) for 250 to 500 µl of sample, most preferably a ratio from 8 to 12 µl of a 1% nanobead suspension (weight/volume) for 450 to 500 µl of sample.

Thus, optimum binding of the pathogenic conformational isomer $PrP^{SC}$ on nanobeads covered with plasminogen may be achieved for example by putting 500 µl of plasma sample in contact with 10 µl of a 1% (weight/volume) suspension of nanobeads (in particular paramagnetic carboxylic nanobeads), covered with an amount of 10 µg of plasminogen/mg of nanobeads, and incubated at 37° C. for two hours.

At the end of step a), the nanobeads covered with plasminogen are separated from the sample (step b)). This step may be applied by collecting the nanobeads by magnetization or centrifugation. Advantageously, the collected beads may be washed.

The thereby collected nanobeads after separation from the sample will bear pathogenic conformational isomer molecules $PrP^{SC}$ bound to the plasminogen, if the analyzed sample comprised $PrP^{SC}$ proteins.

It may be used immediately for proceeding with cyclic amplification of the misfolded prion proteins or be stored under cold conditions, for example at 4° C., before use.

Cyclic Amplification of Misfolded Prion Proteins

Cyclic amplification of misfolded prion proteins is applied by directly using the pathogenic conformational isomer $PrP^{SC}$ bound to the nanobeads via its ligand, the plasminogen.

This amplification is applied by cyclically repeating the steps:

c1) putting said nanobeads obtained in step b) into contact with a preparation comprising said non-pathogenic conformational isomer $PrP^{C}$; and c2) disaggregating the aggregates possibly formed during step c1).

The technology for cyclic amplification of misfolded proteins is known to one skilled in the art and was notably described in International Patent Application WO 2002/004954.

The <<preparation comprising said non-pathogenic conformational isomer $PrP^{C}$>> may for example be a brain or lymphoid tissue homogenate or a biological fluid, such as whole blood, plasma, etc. or a cell lyzate of a healthy individual, preferably from an individual of the same species as the individual from which stems the biological sample to be analyzed (for example a healthy human brain homogenate if a human biological sample is analyzed). The preparation comprising said non-pathogenic conformational isomer $PrP^{C}$ may also be a solution comprising some extracted and optionally purified, or synthetic or recombinant, non-pathogenic conformational isomer $PrP^{C}$.

Advantageously, the non-pathogenic conformational isomer $PrP^{C}$ used may be labeled in a radioactive or fluorescent way, with view to the subsequent detection step.

Preferably, in step c1), the amount of non-pathogenic conformational isomer $PrP^{C}$ used is in excess relatively to the amount of pathogenic conformational isomer $PrP^{SC}$ bound to the nanobeads.

Generally, the initial ratio of non-pathogenic conformational isomer $PrP^{C}$ relatively to the pathogenic conformational isomer $PrP^{SC}$, if it is present, bound to the nanobeads, will be greater than 100:1, preferably greater than 1,000:1 and still preferably greater than 1,000,000:1.

Steps c1) and c2) are preferentially applied under physiological conditions (pH, temperature and ionic force), optionally in the presence of inhibitors of proteases and of detergent. The conditions are preferentially selected so as to allow the pathogenic conformational isomers $PrP^{SC}$, bound to the nanobeads via the plasminogen, to convert the non-pathogenic conformational isomer $PrP^{C}$ into pathogenic conformational isomer $PrP^{SC}$, thereby forming aggregates or oligomers of pathogenic conformational isomers $PrP^{SC}$.

The specific conditions for incubation and the incubation time may be adjusted by one skilled in the art.

For example, step c1) may be applied for 1 minute to 5 days, preferably for 1 minute to 24 hours, preferably for 5 minutes to 6 hours, still preferably for 10 minutes to 4 hours, still preferably for 20 minutes to 2 hours, still preferably for 30 to 90 minutes, still preferably for 30 to 60 minutes. The incubation may be carried out at any temperature, for example at a cold temperature (4-10° C.), at room temperature or at 37° C. It is preferentially applied at 37° C. The incubation may be carried out with stirring (for example from 1 rpm to 1,400 rpm) or without stirring.

The disaggregation step c2) may be carried out by any means known to one skilled in the art, such as treatment with solvents (in the presence of sodium dodecylsulfate (SDS), acetonitrile, dimethylsulfoxide, urea, diluted perfluoroacetic acid, diluted formic acid, etc.), modification of the physico-chemical parameters of the preparation, such as pH, temperature, ionic force, dielectric constant and physical methods such as sonication, laser irradiation, freezing, thawing, French press, incubation in an autoclave, high pressure, mixing, etc. Preferentially, disaggregation is applied by sonication.

Step c2) is carried out so that at least one portion of the aggregates possibly formed during step c1) is disaggregated. The duration of step c2) may be determined by one skilled in the art depending on the disaggregation means used. Step c2) will generally last for between 1 second and 1 hour. A longer duration may however be contemplated. If the disaggregation is carried out by sonication, the duration of step c2) may for example be from 1 second to 10 minutes, preferably from 2 seconds to 5 minutes, preferably from 5 seconds to 2 minutes, preferably from 10 seconds to 1 minute, still preferably from 20 to 40 seconds.

The succession of steps c1) and c2) forms a cycle. For applying the method according to the invention, the steps c1) and c2) are successively applied at least twice, i.e. the method comprises the repetition of at least two cycles.

The number of cycles to be carried out may be determined by one skilled in the art so as to obtain sufficient amplification of the pathogenic conformational isomer $PrP^{SC}$, in order to allow its subsequent detection.

The number of cycles applied in the method concerning the invention may be for example comprised between 2 and 1,000, preferably between 20 and 500, still preferably between 50 and 350, still preferably between 80 and 240.

In particular, step c1) may be applied for 20 minutes to 2 hours, for example for 30 to 120 minutes, or for between 30 and 90 minutes, or further between 30 and 60 minutes, step c2) applied by sonication for 10 seconds to 1 minute, for example for 20 to 40 seconds and the number of cycles may be comprised between 50 and 350, for example between 50 and 100 per amplification round. The disaggregation may be preferentially carried out by means of a Misonix 4000 sonicator, with a power comprised between 60 and 80%.

The optimum amplification conditions in samples of plasma doped with brain homogenates were identified as 30 minutes of incubation, 20 seconds of sonication at 80% power and 80 cycles, this amplification may be repeated if the amount of pathogenic conformational isomer obtained is too low for allowing sensitive detection.

In a very conventional way, the amplification of the protein $PrP^{SC}$ by PMCA applies cycles during which step c1) lasts for 30 minutes.

The inventors however realized that if, in the very first amplification cycle by PMCA, the incubation time of step c1) is only 30 minutes for samples to be analyzed, with extremely little concentrations of protein $PrP^{SC}$, the conversion of the protein $PrP^{C}$ present in the reaction mixture of PMCA (i.e. said preparation comprising the non-pathogenic conformational isomer $PrP^{C}$) may not be sufficient for efficiently initiating amplification by PMCA. In this case, after the disaggregation step c2), it is possible that there remains not enough protein $PrP^{SC}$ capable of ensuring the conformational conversion of the protein $PrP^{C}$, and that finally the protein $PrP^{SC}$ present in the sample cannot be detected. The extension of the duration of step c1) of the very first amplification cycle, for example to about 90 minutes, gives the possibility of setting aside the risk of a false negative result.

Thus, advantageously, the method according to the invention comprises:
a first amplification cycle in which the step c1) is applied for 60 to 120 minutes, preferably for 80 to 100 minutes, still preferably for about 90 minutes, step c2) may be carried out under conditions as described above, preferably by sonication for 10 seconds to 1 minute, more preferably for 20 to 40 seconds, and then
one or several amplification cycles in which the conditions for applying steps c1) and c2) are as described above. For example, step c1) may be applied for 30 to 60 minutes and/or step c2) may be applied by sonication for 20 to 40 seconds. The number of these cycles may be comprised between 49 and 99 per amplification round. The disaggregation may preferentially be carried out by means of a Misonix 4000 sonicator with a power comprised between 60 and 80%.

At the end of the cyclic amplification, the presence or the amount of pathogenic conformational isomer present in the preparation is detected.

Detection

The detection of the pathogenic conformational isomer $PrP^{SC}$ may be preceded with a step d1) for destroying or removing the non-pathogenic conformational isomer $PrP^{C}$, still present in the preparation at the end of step c2). As the pathogenic conformational isomers $PrP^{SC}$ are generally insoluble, even in the presence of a non-denaturating detergent, and resistant to proteases, this step may be typically carried out by treatment with one or several proteases, such as proteinase K, trypsin, etc. or, by centrifugation for separating the insoluble pathogenic conformational isomers $PrP^{SC}$ from the soluble non-pathogenic conformational isomers.

The detection of pathogenic conformational isomer $PrP^{SC}$ present in the preparation, optionally treated as indicated in step d1), may be carried out by any suitable method. As non-limiting examples, the following detection methods may be used:

electrophoresis on polyacrylamide gel (SDS-PAGE) followed by Western blotting;

an immunotest, in particular direct, indirect ELISA, or of the sandwich type, using antibodies directed against the prion protein, preferably specific to the pathogenic conformational isomer;

radioactive or fluorescent tests: by using a labeled (radioactively with $^{3}H$, $^{14}C$, $^{35}S$, $^{125}I$, etc., or in a fluorescent way with any suitable fluorophore) non-pathogenic conformational isomer for the cyclic amplification, it is possible to obtain by a conformational transition, some labeled neoformed pathogenic conformational isomer $PrP^{SC}$ which may be detected and quantified;

the use of protein chips, velocimetric sensors, electrochemical biosensors, etc.

As an illustration, the detection of the protein $PrP^{SC}$ may be carried out as described in Example 1 by SDS-PAGE separation and immunoblotting by means of monoclonal anti-PrP antibodies (for example the human monoclonal anti-PrP 3F4 antibody or the ovine monoclonal anti-PrP 6D11 antibody).

The detection of the presence of said pathogenic conformational isomer $PrP^{SC}$ in the preparation is indicative of the presence of the pathogenic conformational isomer $PrP^{SC}$ in the analyzed sample.

When the method according to the invention is applied on a biological sample from a subject, the detection of the presence of said pathogenic conformational isomer in step d) is indicative of a prion disease or transmissible spongiform encephalopathy (TSE) in the subject. The method is then a method for in vitro diagnostic of a TSE disease. If the sample is a sample taken for example from blood, plasma or from an organ, the detection of the presence of said pathogenic conformational isomer $PrP^{SC}$ in step d) then indicates that the blood or plasma sample is unsuitable for transfusion, or that the organ is unsuitable for transplantation, since it is potentially infectious as a vector of TSE.

When the method according to the invention is applied on a sample which is a food fluid or solid, the detection of the presence of said pathogenic conformational isomer $PrP^{SC}$ in step d) is indicative of a sample contaminated by the pathogenic conformational isomer PrPSC, unsuitable for consumption since it is potentially infectious as a vector of TSE.

Step d) may comprise the quantification of said pathogenic conformational isomer $PrP^{SC}$.

Kit for Detecting a Pathogenic Conformational Isomer of the Prion Protein

The invention also relates to a kit for applying the method according to the invention.

Such a kit may comprise:
nanobeads, preferably paramagnetic nanobeads;
plasminogen, preferably human plasminogen
optionally another type of ligand of the pathogenic conformational isomer of the prion protein;
a known amount of the non-pathogenic conformational isomer $PrP^C$;
and optionally instructions for applying a method such as described above.

Preferably, said kit comprises nanobeads already covered with plasminogen and optionally with said at least one type of ligand of the pathogenic conformational isomer $PrP^C$.

The kit may further comprise at least one disaggregation means, such as for example at least one solvent or a physical disaggregation device such as a sonicator, a laser, etc.

The kit may further comprise at least one detection means such as one or several antibodies directed against the prion protein, preferably at least one specific antibody of the pathogenic conformational isomer.

The instructions contained in the kit may in particular specify how to apply the succession of the steps for capturing the pathogenic conformational isomer, for cyclic amplification of the misfolded proteins and for detection.

Method for Decontaminating a Biological Sample

Nanobeads covered with plasminogen may also be used for capturing the prion proteins $PrP^{SC}$ present in a biological sample so as to decontaminate it by getting rid of the proteins $PrP^{SC}$ which it contains.

The invention thus also relates to a method for decontaminating a biological sample which may contain some pathogenic conformational isomer of the prion protein ($PrP^{SC}$), said method comprising the steps:

a) putting nanobeads, preferably paramagnetic nanobeads covered with plasminogen into contact with a sample;
b) separating said paramagnetic nanobeads covered with plasminogen from the sample;
c) collecting the thereby decontaminated sample.

In step a) of this method, the nanobeads covered with plasminogen are put into contact with the sample to be analyzed and incubated in contact with the sample for sufficient time and under conditions allowing all the pathogenic conformational isomers $PrP^{SC}$ present in the sample to bind to the plasminogen.

The incubation time and conditions may be variable depending on the nature of the sample.

Incubation may be carried out at any temperature, for example at a cold temperature (4-10° C.), at room temperature or at 37° C. It is preferentially applied at 37° C. The incubation may be carried out with stirring (for example from 1 rpm to 1,400 rpm) or without stirring. The incubation may be carried out for a duration from 1 minute to 5 days, preferably for 10 minutes to 24 hours, preferably 30 minutes to 8 hours, preferably 1 to 4 hours, still preferably from 2 hours to 3 hours. The incubation time may be adjusted depending on the respective amounts of pathogenic conformational isomer of the prion protein in the sample and of plasminogen bound on the solid support.

The nanobeads covered with plasminogen may be separated from the sample (step b)) for example by collecting the nanobeads by magnetization if the beads are paramagnetic or by centrifugation.

The decontamination of the thereby treated biological sample may be checked by applying a method for in vitro detection of a pathogenic conformational isomer of the prion protein ($PrP^{SC}$) in a sample as defined above, so as to make sure that the pathogenic conformational isomer of the prion protein is absent in the sample.

The definitions and conditions described in connection with the method for detecting a pathogenic conformational isomer of the prion protein according to the invention, are also applicable to the kit for detecting a pathogenic conformational isomer of the prion protein and to the method for decontaminating a sample defined above.

The invention will be described in more detail considering the following examples.

EXAMPLES

Example 1

Materials and Methods

Preparation of the Samples

Whole blood of human volunteers was sampled in collecting tubes containing EDTA (Etablissement Français du Sang—Pyrénées, Méditerranée) after having obtained informed consent of each blood donor in writing, in accordance with French law (Code de la santé publique, article L. 1243-3). The plasma was then isolated and collected after centrifugation at 1,500 g for 15 minutes at room temperature.

Whole blood was collected from four healthy sheep and from four sheep naturally infected with scrapie, in the terminal stage of the disease (INRA/Ecole Nationale Vétérinaire de Toulouse—France). The sheep expressed the allele V136R154Q171 of ovine PrP. Sheep White Blood Cells (SWBC) were prepared from the leukocyte layer obtained after centrifugation at 2,000 g for fifteen minutes at room temperature. The residual red cells were removed from the leukocyte layer by lysis in 155 mM $NH_4Cl$, 10 mM $KHCO_3$, 1 mM EDTA (pH 8) for 20 minutes on ice, followed by centrifugation at 1,500 g for 10 minutes at 4° C. The SWBCs were then washel with PBS at pH 7.4 and aliquots of $10^7$ SWBCs clarified by PBS were stored at −80° C.

Doped plasmas were prepared as follows: 500 μl of plasma from healthy human donors were doped with decimal serial dilutions (from $10^{-3}$ to $10^{-11}$) either of homogenates of brain infected by the variant of Creutzfeldt-Jacob's disease (vCJD), or of homogenates of brain infected with scrapie (strain 127S) from ovine transgenic mice (line tg338). The infected brain homogenates (IBH) were prepared at 10% (weight/volume) in 5% glucose (i.e. a dilution of $10^{-1}$).

Capture of the Prion Protein

Covering Magnetic Beads with Human Plasminogen (Pig)

According to studies published by Fischer et al. (*Nature*, 2000, 408 (6811): 479-483), human plasminogen was used as an efficient ligand for capturing prion proteins. Nanomagnetic carboxylic beads (Ademtech France) were covered and stored according to instructions of the manufacturer. Briefly, the beads were covered with human plasminogen (Fluka Sigma-Aldrich) by stirring for 2 hours at 37° C. The optimum amount of ligand to be used was evaluated by testing three plasminogen concentrations: 10, 20 and 30 µg/mg of beads, 10 µg/mg of beads being the lowest concentration recommended by the manufacturer. After a blocking step at 37° C. with a 0.5 mg/ml albumin solution, the beads were stored at 4° C. in the Ademtech storage solution.

Capture of the Prion Protein by Nanobeads Covered with Plasminogen

Doped plasmas (500 µl) were mixed volume to volume with a lysis/binding buffer (LB buffer: PBS 2×, 6% NP40, 6% Tween 20) before incubation with beads covered with plasminogen at room temperature for 90 minutes. The amount of beads to be used for each sample was evaluated by testing different conditions (2.5, 5, 10, 20, 30, 40, 60 and 90 µl of 1% plasminogen beads). After a step of washing with PBS, the magnetic beads were isolated for subsequent PMCA amplification.

For capturing $PrP^{TSE}$ from the SWBCs, the cells were first incubated on ice for 30 minutes with a 500 µl of LB buffer. After centrifugation at 1,000 g at 4° C. for 2 minutes, the supernatant was collected and mixed with 500 μl of LB buffer before incubation with the nanobeads covered with plasminogen as described above.

PMCA (Protein Misfolding Amplification Assay)

Preparation of the PMCA Substrates:

The normal brain homogenates (NBH) of transgenic mice either for human PrP (allele $M^{129}$, line tg650) (Beringue et al., PLoS One 2008, 3 (1):e1419) or for ovine PrP (allel VRQ, line tg338) (Laude et al., C. R. Biol. 2002, 325 (1):49-57) were used as a $PrP^{C}$ substrate for PMCA. The brains were collected from animals euthanized with $CO_2$ and perfused with PBS containing 5 mM of EDTA. The brains were rinsed in cold PBS and immediately frozen on dry ice before long term storage at −80° C. The brains were then homogenized at a concentration of 10% (weight/volume) with the lysis/conversion buffer (CB buffer) consisting of 150 mM NaCl, 1% Triton X-100, a cocktail of protease inhibitors (Roche) in PBS (pH 7.2). The homogenates were centrifuged at 2,000 g for 20 seconds in order to remove most of the brain materials. The supernatant was frozen at −80° C. in single-use aliquots until their use.

PMCA

The captured prion protein was mixed with 90 μl of 10% NBH. Next, automatic amplification by PMCA was applied by using the Misonix 4000 instrument (Misonix, N.Y., USA). Each cycle consisted of an incubation step (37° C.) and of a sonication step. First, the following PMCA parameters had been optimized: incubation time per cycle (30 and 60 minutes, or further 90 minutes for the first cycle), sonication time per cycle (20 and 40 seconds), power level (60, 70, 80%) and number of PMCA cycles (50, 80, 100) per round. Following the first PMCA round, the reaction product is diluted in fresh substrate (1/10) and PMCA is repeated. This technique is known as serial PMCA (sPMCA). The product of this second PMCA round may further be diluted and subject to PMCA, and so forth, allowing indefinite amplification of $PrP^{TSE}$.

Digestion by Proteinase K (PK)

The amplified products (18 μl samples) were digested with PK at 200 μg/ml for one hour at 45° C. The reaction was stopped by adding phenyl methyl sulfinide fluoride 5 mM. The samples were then denaturated at 100° C. in a sample buffer SDS-PAGE (2% SDS, 100 mM Tris/HCl pH 7.4 and 0.5% bromophenol blue) and stored at −80° C.

SDS-PAGE and Immunoblots

The protein samples were set to migrate on 12% NUPAGE gels (Invitrogen, Cergy-Pontoise, France) at 200 volts and electro-transferred onto PVDF membranes (Millipore, Molsheim, France). After blocking with 5% skimmed milk in a 0.05% TBS-Tween 20 buffer, the transfers were probed with anti-PrP monoclonal antibodies (MAb), 3F4 Mab or 6D11 MAb (Signet/Proteogenix, Illkirch, France) for detecting human and ovine prion protein respectively.

The transfers were developed by using a secondary mouse anti-IgG antibody bound to peroxidase and the chemiluminescent substrate Luminol (ECL reagent, Amersham Bioscience, France).

Materials from the National Institute for Biological Standards and Control (NIBSC)

NIBSC made available a series of reference reagents prepared from brain specimens from post-mortem humans (www.nibsc.ac.uk/cjd/brainsamples.html). The brain reference reagents were obtained from the CJD Resource Centre in the form of 10% (weight/volume) homogenates in 0.25 M saccharose.

Two panels were tested. Panel 1 consisted of 20 negative plasma samples including 10 randomly selected plasmas distributed as duplicates. Panel 2 was a blind panel consisting of vCJD brain dilution duplicates in normal plasma, and of negative controls including normal brain added in plasma and negative plasma alone (4 series of 24 tubes numbered from A to X).

Example 2

Optimization of the Capture Technology Based on Plasminogen/sPMCA by Using Brain Material Infected by Scrapie The PMCA parameters were optimized by using normal brain homogenates and infected by scrapie from transgenic mice for the ovine PrP (allele VRQ, line tg338) for the PMCA reaction. PMCA was first evaluated by crossing the parameters: number of cycles, incubation, sonication and power of the Misonix. A 80-cycle PMCA round (30 minute incubation, 20 second sonication, 80% power) allowed detection of $PrP^{TSE}$ in the $10^{-8}$ IBH dilution by immunoblotting (n=3 from 2 different IBHs). The observed signal level was similar to the one obtained for the $10^{-3}$ non-amplified dilution, indicating a 5 log amplification level by the first PMCA round. When the amplified samples were diluted 10 times in fresh NBH and subject to a second PMCA 80-cycle round, a specific $PrP^{TSE}$ detection signal was detected reproducibly down to a dilution of $10^{-10}$ (n=3 from 2 different IBHs), indicating 7 log amplification. No signal was detected with non-infected brains, amplified in a similar way (n=3 from 2 different IBHs).

As PMCA was optimized, the capture parameters for $PrP^{TSE}$ nanobeads covered with plasminogen were then optimized (plasminogen concentration and bead volume). A $10^{-4}$ dilution of IBH with scrapie was diluted in human plasma (500 μl) and mixed with different volumes of beads with different plasminogen concentrations before PMCA amplification. The strongest $PrP^{TSE}$ signal was observed when the lowest plasminogen concentration, at 10 μg plasminogen/mg of beads, and the smallest volume of beads, 10 μl/500 μl of doped plasma were used.

By using these conditions, $PrP^{TSE}$ was able to be detected in $10^{-6}$ IBH dilutions added into 500 μl of human plasma. The obtained signal appeared to be similar to the one obtained when a $10^{-6}$ IBH dilution was directly used for sowing the PMCA substrate, suggesting that the capture step by the nanobeads covered with plasminogen was efficient. Both negative controls (500 µl of human plasma mixed with nanobeads covered with plasminogen before PMCA) remained negative.

Example 3

Validation of the Combined Test of Nanobeads Covered with Plasminogen/sPMCA on a Blood Panel of Healthy and Infected Sheep It was then checked that the experimental conditions used allowed specific detection of PrP$^{TSE}$ in SWBCs infected by scrapie. After a PMCA round (80 cycles), no specific PrP$^{TSE}$ signal was detected by immunoblotting 4 samples infected with SWBC. After a second round, one of the 4 infected SWBCs exhibited a positive signal. After a third PMCA round, a strong PrP$^{TSE}$ signal was detected in the totality of the 4 infected SWBCs, while in the SWBC samples from healthy sheep, no signal was detected. The detection of the SWBCs of sheep infected by scrapie and negative SWBCs was reproduced 3 times.

By comparison, the application of the sPMCA method on SWBC infected by scrapie, without any preliminary capture step, did not allow detection of the PrP$^{TSE}$ protein.

Example 4

Evaluation and Validation of the Nanobeads Covered with Plasminogen/sPMCA Test on Human Samples Similar optimizations of PMCA were applied by using the vCJD human brain homogenates and normal brain homogenates from transgenic mice for human PrP (allele M$^{129}$, line tg650), as described for ovine PMCA, and the parameters giving the optimum amplification for human PMCA were identified as being exactly the same (80 cycles, 30 minutes of incubation, 20 seconds of sonication, power of 80%).

After capture of PrP$^{TSE}$ in human plasmas doped by adding vCJD IBH 1/10 dilutions ($10^{-5}$ to $10^{-9}$), a first PMCA round allowed detection of the protein in $10^{-6}$ IBH dilutions. This indicated about 3 log amplification as compared with the signal obtained from non-amplified $10^{-3}$ dilution.

After 1/10 dilution of the amplified samples with fresh NBHs, a second and third round of 80 cycles of PMCA were carried out. This allowed detection of a specific PrP$^{TSE}$ signal down to dilutions of $10^{-7}$ and $10^{-9}$ respectively, indicating a 4 and 6 log amplification factor. The sensitivity of the tests was confirmed by repeating this test from 3 different IBHs, one of them being the NIBSC panel "blue capped brain tissue vCJD codon 129M/M" (Ref NHBY0/0003).

This test combining plasminogen-based capture of the prion in human blood samples and PMCA amplification was then evaluated by testing panels provided by NIBSC. All the samples of panel 1 (negative samples) were tested as negative (20/20) leading to 100% specificity.

The results of the blind analysis of the 80 samples of panel 2 were analyzed by the NIBSC committee and a $10^{-5}$ dilution sensitivity for vCJD brain homogenates added into the plasma was obtained (Table 1). The 32 control samples of panel 2 were all tested as negative and confirmed the 100% specificity (total 52/52).

TABLE 1

Evaluation of the detection test of PrP$^{TSE}$ on a human blind panel (NIBSC)

| Biological material | Dilutions | Positive |
|---|---|---|
| Plasma doped with vCJD brain | $10^{-2}$ | 4/4 |
| | $10^{-3}$ | 4/4 |
| | $10^{-4}$ | 4/4 |
| | $10^{-5}$ | 3/8 |
| | $10^{-6}$ | 1/4 |
| | $10^{-7}$ | 0/4 |
| | $10^{-8}$ | 0/8 |
| Plasma doped with vCJD rat | $10^{-1}$ | 4/4 |
| | $10^{-2}$ | 0/4 |
| | $10^{-3}$ | 0/8 |
| | $10^{-4}$ | 0/4 |
| | $10^{-5}$ | 0/4 |
| Plasma doped with control brain | $10^{-2}$ | 0/4 |
| | $10^{-3}$ | 0/4 |
| | $10^{-4}$ | 0/4 |
| Plasma doped with control rat | $10^{-1}$ | 0/4 |
| | $10^{-2}$ | 0/4 |
| Control plasma | — | 0/16 |
| Positive total | | 20/96 |

The invention claimed is:

1. An in vitro method for detection of a pathogenic conformational isomer of the prion protein (PrP$^{SC}$) in a sample, said method comprising the steps consisting of:
  a) putting nanobeads covered with plasminogen into contact with a sample;
  b) separating said nanobeads covered with plasminogen bearing the possibly present PrP$^{SC}$, from the sample;
  c1) putting said nanobeads covered with plasminogen bearing the possibly present PrP$^{SC}$ obtained in step b) in contact with a preparation comprising some non-pathogenic conformational isomer of the prion protein (PrP$^c$);
  c2) disaggregating the aggregates possibly formed during step c1);
  d) detecting the presence of PrP$^{SC}$ in the preparation, the presence of PrP$^{SC}$ in the preparation being indicative of the presence of PrP$^{SC}$ in the sample;
  the steps c1) and c2) forming a cycle which is repeated at least twice before applying step d).

2. The in vitro method according to claim 1, wherein step d) is preceded with a step d1) for destroying or removing the protein PrP$^c$ present in the preparation at the end of step c2).

3. The in vitro method according to claim 1, wherein nanobeads are paramagnetic nanobeads.

4. The in vitro method according to claim 3, wherein the paramagnetic nanobeads are covered with plasminogen in an amount from 10 to 30 µg of plasminogen/mg of paramagnetic nanobeads.

5. The in vitro method according to claim 1, wherein the nanobeads covered with plasminogen are put into contact with the sample in step a) at a ratio from 2.5 to 90 µl of 1% (weight/volume) nanobead suspension for 50 to 500 µl of sample.

6. The in vitro method according to claim 1, wherein step a) is carried out with stirring.

7. The in vitro method according to claim 1, wherein disaggregation of step c2) is carried out by sonication.

8. The in vitro method according to claim 1, wherein step c1) is applied for 20 minutes to 2 hours and step c2) is carried out by sonication for 10 seconds to 1 minute.

9. The in vitro method according to claim 1, which comprises the steps consisting of:

a) putting the paramagnetic nanobeads covered with plasminogen into contact with a sample, in an amount from 10 to 30 μg of plasminogen/mg of paramagnetic nanobeads;

b) separating said paramagnetic nanobeads covered with plasminogen bearing the possibly present $PrP^{sc}$, from the sample;

c1) putting said paramagnetic nanobeads covered with plasminogen bearing the possibly present $PrP^{sc}$ obtained in step b) into contact for 20 minutes to 2 hours with a preparation comprising some non-pathogenic conformational isomer of the prion protein ($PrP^{c}$);

c2) disaggregating by sonication the aggregates possibly formed during step c1) for 10 seconds to 1 minute;

d) detecting the presence of $PRP^{sc}$ in the preparation, the presence of $PrP^{sc}$ in the preparation being indicative of the presence of $PrP^{sc}$ in the sample;

steps c1) and c2) forming a cycle which is applied from 50 to 350 times before applying step d).

10. The in vitro method according to claim 1, which comprises:

a first amplification cycle in which step c1) is applied for 60 to 120 minutes, and then one or several amplification cycles in which step c1) is applied for 30 to 60 minutes.

11. The in vitro method according to claim 10, which comprises:

a first amplification cycle in which step c1) is applied for 60 to 120 minutes, and step c2) is applied by sonication for 10 seconds to 1 minute, and then one or several amplification cycles in which step c1) is applied for 30 to 60 minutes.

12. The in vitro method according to claim 10 which comprises:

a first amplification cycle during which step c1) is applied for 80 to 100 minutes, and step c2) is applied by sonication for 20 to 40 seconds, and then 49 to 99 amplification cycles during which step c1) is applied for 30 to 60 minutes, and step c2) is applied by sonication for 20 to 40 seconds.

13. The in vitro method according to claim 1, wherein said sample is a biological sample from a subject and the detection of the presence of $PrP^{SC}$ in step d) is indicative of a transmissible spongiform encephalopathy disease in the subject.

14. The in vitro method according to claim 13, wherein the transmissible spongiform encephalopathy is Creutzfeld Jacob's disease or its variant.

15. The in vitro method according to claim 1, wherein said sample is a food fluid or solid and the detection of the presence of $PrP^{SC}$ in step d) is indicative of a food fluid or solid contaminated by the pathogenic conformational isomer $PrP^{SC}$.

16. The in vitro method according to claim 1, in which said sample is or stems from a sample taken from blood, plasma or from an organ and the detection of the presence of $PrP^{SC}$ in step d) is indicative of a sample taken from blood or plasma unsuitable for transfusion, or from an organ unsuitable for transplantation.

17. The in vitro method according to claim 1, wherein step d) comprises the quantification of said pathogenic conformational isomer.

18. A kit comprising:

paramagnetic nanobeads;

plasminogen;

a known amount of the non-pathogenic conformational isomer of the prion protein;

optionally instructions for applying a method according to claim 1.

* * * * *